United States Patent [19]

Eckenhoff

[11] Patent Number: 4,643,731
[45] Date of Patent: Feb. 17, 1987

[54] MEANS FOR PROVIDING INSTANT AGENT FROM AGENT DISPENSING SYSTEM

[75] Inventor: James B. Eckenhoff, Los Altos, Calif.

[73] Assignee: ALZA Corporation, Palo Alto, Calif.

[21] Appl. No.: 766,454

[22] Filed: Aug. 16, 1985

[51] Int. Cl.⁴ .............................................. A61K 9/22
[52] U.S. Cl. ................................. 604/892; 424/19
[58] Field of Search ............................ 604/890–892, 604/893–897; 424/15–21, 117; 427/3

[56] References Cited

U.S. PATENT DOCUMENTS

| Re. 31,764 | 12/1984 | Voss et al. ...................... | 427/3 |
|---|---|---|---|
| 2,099,402 | 11/1937 | Keller .............................. | 424/21 |
| 2,340,037 | 1/1944 | Zipper ............................. | 167/83 |
| 3,056,724 | 10/1962 | Marston .......................... | 604/892 |
| 3,312,594 | 4/1967 | Cyr et al. ........................ | 424/117 |
| 3,608,549 | 9/1971 | Merrill ............................ | 604/891 |
| 3,732,865 | 5/1973 | Higuchi et al. ................. | 128/260 |
| 3,760,804 | 9/1973 | Higuchi et al. ................. | 128/260 |
| 3,769,895 | 9/1973 | Higuchi ........................... | 128/260 |
| 3,845,770 | 11/1974 | Theeuwes et al. .............. | 128/260 |
| 3,929,132 | 12/1975 | Higuchi ........................... | 128/260 |
| 3,995,632 | 12/1976 | Nakano et al. ................. | 128/260 |
| 4,034,756 | 7/1976 | Higuchi et al. ................. | 128/260 |
| 4,088,864 | 5/1978 | Theeuwes et al. .............. | 219/121 |
| 4,111,202 | 9/1978 | Theeuwes ....................... | 604/893 |
| 4,178,361 | 12/1979 | Cohen et al. ................... | 424/22 |
| 4,196,187 | 4/1980 | Dannelly et al. ............... | 424/21 |
| 4,200,098 | 4/1980 | Ayer et al. ...................... | 128/260 |
| 4,235,236 | 11/1980 | Theeuwes ....................... | 128/260 |
| 4,285,987 | 8/1981 | Ayer et al. ...................... | 427/3 |
| 4,298,003 | 11/1981 | Theeuwes et al. .............. | 604/892 |
| 4,327,725 | 5/1982 | Cortese et al. ................. | 604/893 |
| 4,439,196 | 3/1984 | Higuchi ........................... | 604/890 |
| 4,475,916 | 10/1984 | Himmelstein .................. | 604/890 |

FOREIGN PATENT DOCUMENTS

| 19250 | 3/1972 | Australia . |
| 2729068 | 11/1979 | Fed. Rep. of Germany . |
| 1540258 | 9/1968 | France . |

Primary Examiner—C. Fred Rosenbaum
Assistant Examiner—Jerome R. Smith, Jr.
Attorney, Agent, or Firm—Paul L. Sabatine; Edward L. Mandell; Steven F. Stone

[57] ABSTRACT

A dispensing system is disclosed for delivering a beneficial agent formulation instantly and continuously over time to an environment of use. The dispensing system comprises an outer housing surrounding at least a part of a dispensing device. The dispensing device comprises a wall surrounding a compartment with a passageway in the wall connecting the compartment with the interior of the dispensing device. A beneficial agent formulation is present in the housing for instant delivery and a beneficial agent formulation is present in the compartment for continuous delivery.

12 Claims, 8 Drawing Figures

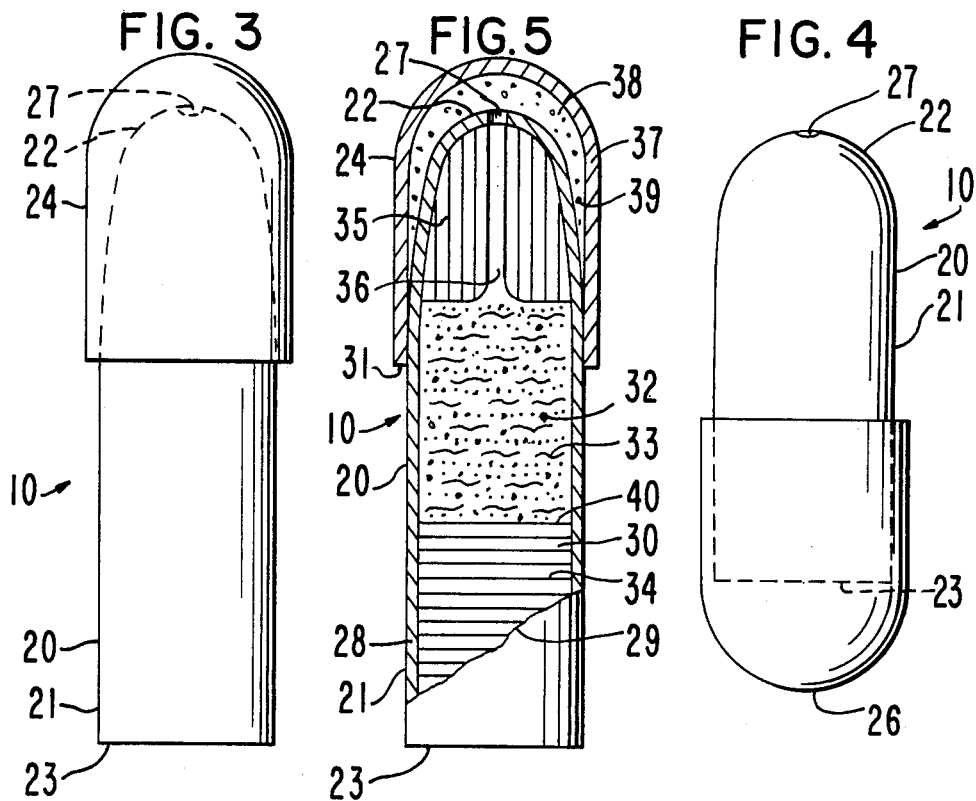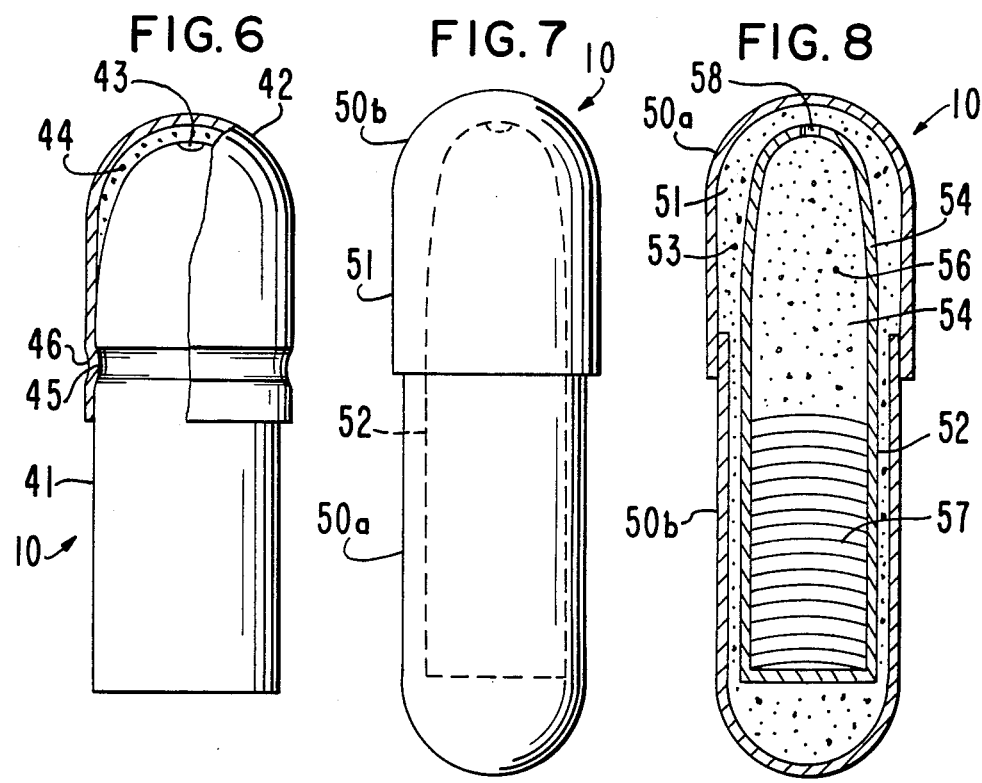

MEANS FOR PROVIDING INSTANT AGENT FROM AGENT DISPENSING SYSTEM

FIELD OF THE INVENTION

This invention pertains to an agent dispensing system comprising means for providing instant agent to an agent receptor environment. The agent dispensing system provides a pre-programmed, unattended delivery of a beneficial agent, that is delivered instantly in a beneficially effective amount, followed by continuous delivery of the agent in a beneficially effective amount over a prolonged period of time. The dispensing system is manufactured in the form of a dispensing device for the instant and the continuous delivery of agent to a selected receptor site.

BACKGROUND OF THE INVENTION

Agent dispensing systems, manufactured in the form of dispensing devices, for the precision administration of agents with controlled delivery patterns and with extended operational delivery times are known to the dispensing art in the U.S. Pat. Nos. 3,845,770 and 3,916,899, both issued to inventors Theeuwes and Higuchi, and in the U.S. Pat. No. 4,350,271 issued to inventor Eckenhoff. In these patents, the dispensing devices disclosed comprise a semipermeable wall that surrounds a compartment containing an agent formulation that is dispensed from the device under the influence of (1) an osmotically active solute, or (2) an osmotically active swellable polymer. These dispensing devices are extraordinarily effective for delivering an agent that possesses degrees of solubility, from poorly soluble to very soluble, in aqueous and biological fluids.

The above dispensing devices represent outstanding and pioneering advancements in the dispensing art, and they are useful for dispensing innumerable agents to various environments of use. Now, it has been discovered these dispensing devices can be improved further by enhancing the agent delivering kinetics and the usefulness of the devices. That is, it has now been discovered unexpectedly that dispensing systems can be provided that initially deliver bio-affecting agent followed by a substantially constant amount of agent at a controlled rate over time; thereby making agent instantly available to an agent receptor by substantially eliminating the startup agent delivery time frequently required to deliver agents from these dispensing devices. The dispensing systems made available by the invention embody a unique initial agent delivery followed by controlled and constant prolonged delivery, thereby functioning according to a preselected, built-in optimal program of agent presentation.

OBJECTS OF THE INVENTION

Accordingly, in view of the above presentation, it is an immediate object of this invention to provide a dispensing system that initially delivers an effective amount of agent followed by a continuous delivery of agent over a prolonged period of time;

Another object of this invention is to provide a dispensing system comprising a first means containing agent that is available for instant delivery and a second means containing agent that is available for continuous delivery, thereby providing a dispensing system that delivers agent immediately and continuously when in operation in an environment of use;

Another object of the invention is to provide a dispensing system comprising a first carrier means for supplying an agent positioned on the exterior of a second means for supplying agent, which first carrier means contains an agent that is available for immediate delivery as a burst of agent for substantially eliminating the startup time associated with the second means;

Another object of the invention is to provide a dispensing system manufactured in the form of a dispensing device which comprises an outermost member housing an agent formulation that is available for immediate delivery, thereby making the agent formulation available for performing its beneficial effects;

Another object of the invention is to provide a dispensing device adapted for administering an agent formulation to an animal comprising an outer housing for delivering an initial agent-pulse which acts in cooperation with the dispensing device that follows with continuous agent delivery at a rate controlled by the dispensing device over time;

Another object of the invention is to provide an improvement over the prior art by making available a dispensing device possessing instant agent availability during the startup period of time the prior art dispensing devices did not make agent available to an agent receptor; and, Another object of the invention is to provide an improvement in an agent dispensing device by providing a dispensing device that is easy to manufacture and inexpensive to use, and also makes instant agent available followed by constant agent availability over time;

Other objects, features and advantages of the invention will be more apparent to those skilled in the art from the following detailed specification, taken in conjunction with the drawings and the accompanying claims.

BRIEF DESCRIPTION OF THE DRAWING FIGURES

In the drawing figures, which are not drawn to scale, but are set forth to illustrate various embodiments of the invention, the drawing figures are as follows:

FIG. 3 is a view of a dispensing system comprising a first means for providing instant agent and made as a single piece adapted to fit snuggly over a second means comprising an osmotic device that delivers agent after the first means delivers agent;

FIG. 4 is a view of the dispensing system of FIG. 3 with the instant agent available means surrounding and encapsulating the rear end of the osmotic device of FIG. 3;

FIG. 5 is an opened view of the dispensing system of FIG. 3 depicting the instant agent available delivery member in structural harmony with the delivery device that follows the instant agent deliver with continuous agent delivery over time;

FIG. 6 is a view of the dispensing system of FIG. 3 depicting another embodiment comprising a snap-over cap for engaging the dispensing device and for storing an agent available for instant use;

Figure 1:
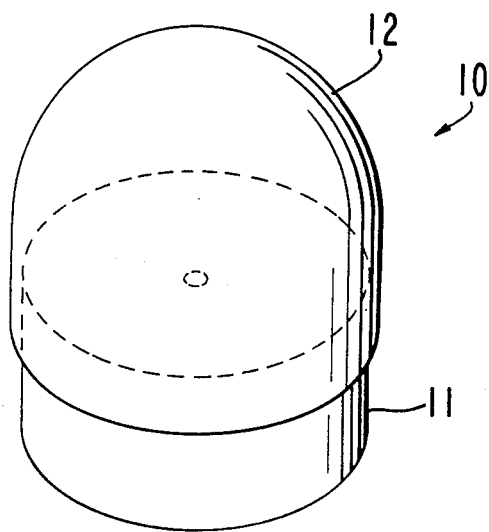
FIG. 1 is a view of a dispensing system comprising two parts, an osmotic dispensing device having a portion telescopically capped by an engaging cap portion.

FIG. 7 is a view of a dispensing system comprising in combination (1) a capsule made of two parts comprising a body portion telescopically capped by an engaging cap portion to define an internal space for containing (2) both free agent and an agent delivery device; and, FIG. 8 is an opened view of the dispensing system of FIG. 7 illustrating the capsule formed of two parts, and both free agent available for instant release and agent contained in the dispensing device available for follow-up release over time.

In the drawings and in the specification, like parts in related figures are identified by like parts. The terms appearing earlier in the specification and in the description of the drawing figures, as well as embodiments thereof are further detailed elsewhere in the disclosure.

DETAILED DESCRIPTIONS OF THE DRAWING FIGURES

Turning now to the drawing figures in detail, which figures are examples of dispensing systems provided by the invention, and which examples are not to be construed as limiting, one example of a dispensing system is seen in FIG. 1 identified by the numeral 10. In FIG. 1, dispensing system 10 is seen comprising two parts, or dispensing device 11 and a cap member 12. Cap member 12 is made for slipping over and releasably engaging and capping a part of dispensing device 11.

Figure 2:
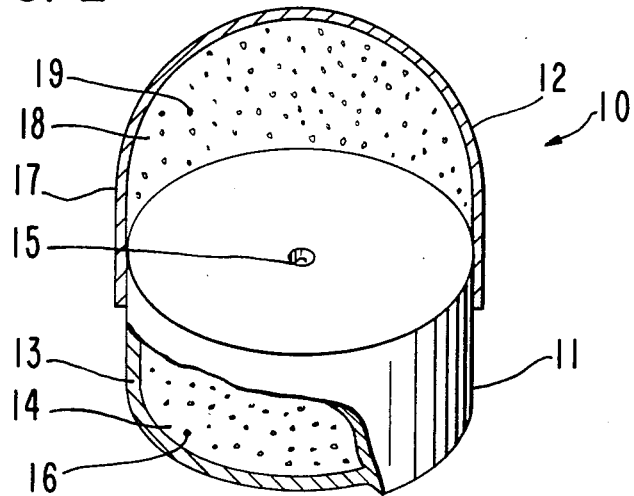
FIG. 2 is an opened view of FIG. 1 of the telescopically capped portion depicting drug available for instant delivery in the engaging cap, and an opened view of the osmotic device depicting agent available for continuous delivery over time.

FIG. 2 depicts dispensing system 10 of FIG. 1 with dispensing device 11 and cap 12 in opened view for illustrating the structural members comprising dispensing system 10. In FIG. 2, dispensing device 11 is an osmotic dispensing device and it comprises wall 13 surrounding internal compartment 14 and osmotic passageway 15. Wall 12 is formed of a nontoxic polymeric composition that is totally, or in at least a part, permeable to the passage of an external fluid and it is substantially impermeable to the presence of an agent formulation 16 present in compartment 14. The polymeric composition forming wall 13 is inert and it maintains its physical and chemical integrity driving the dispensing life of osmotic dispensing device 11. Typical materials for forming wall 13 include semipermeable polymers known to the dispensing art as osmosis and reverse osmosis membranes. These polymeric compositions include cellulose ester, cellulose ether, cellulose ester-ether, cellulose acylate, cellulose diacylate and cellulose triacylate.

Internal compartment 14 of device 10 contains a beneficial agent formulation 16. Agent formulation 16 can comprise in one embodiment agent 16 neat that is soluble in an external fluid and exhibits an osmotic pressure gradient across semipermeable wall 13 against an external fluid; or, in another embodiment when agent 16 has limited solubility in the external fluid it can be mixed with an osmagent that is soluble in the external fluid and exhibits an osmotic pressure gradient across wall 13 against an external fluid.

Cap member 12 comprises a wall 17 that surrounds and defines an internal space 18 for containing a beneficial agent formulation 19. Agent formulation 19 is available for instant release to an environment of use. Wall 17 is formed of a non-toxic wall forming material that in a presently preferred embodiment is hydrophilic and undergoes hydrolysis, dissolves, dissolution, or the like, in an aqueous or biological fluid. This property of wall 17 causes wall 17 to loose its integrity thereby making cap member 17 release immediately agent formulation 19 to an environment of use. Typical materials for forming wall 17 include gelatin, more particularly gelatin having a viscosity of 15 to 30 millipoises and a bloom strength up to 150 grams; gelatin having a bloom value of 160 to 250; pectin having a molecular weight ranging from 30,000 to 3,000,000; zein available as prolamine, and the like.

In operation, dispensing system 10 releases a beneficial agent instantly and then continuously by coordinated operations in the environment of use. Then, cap member 12 in the presence of fluid in the environment of use dissolves and instantly releases agent formulating 19 to the environment of use. This first operation exposes all of dispensing device 11 to the environment of use. Concomitantly, dispensing device 11 imbibes fluid through semipermeable wall 13 into compartment 14 in a tendency towards osmotic equilibrium at a rate determined by the permeability of wall 13 and the osmotic pressure gradient across wall 13. The imbibed fluid continuously forms a solution containing active agent 16, or a solution of osmagent containing active agent 16 in suspension, which solution or suspension, in either instance, is hydrodynamically dispensed through passageway 15 by the operations of dispensing device 11. Dispensing system 10, by the combined operations of cap member 12 and dispensing device 11, provides instant agent formulation followed by continuous agent formulation over time to the environment of use.

FIG. 3 and FIG. 4 both depict another dispensing system 10 provided by this invention. Dispensing system 10 of FIG. 3 and FIG. 4 pertains to an elongated, cylindrical shaped dispensing, system 10 adapted and sized for administering a beneficial agent to a warm-blooded animal, and more particularly a ruminant. In FIG. 3, dispensing system 10 comprises dispensing device 20 having body 21, lead end 22, trailing end 23 and a portion of lead end 22 surrounded and endorsed by cap member 24. FIG. 4 depicts dispensing device 20 comprising body 21, lead end 22, trailing end 23, and a portion of trailing end 23 surrounded and enclosed by rear cap 26. In both FIGS. 3 and 4, dispensing device 20 is provided with a passageway 27 that connects the exterior of dispensing device 20 with the interior of dispensing device 20.

FIG. 5 is an opened view of dispensing system 10 of FIG. 3. Dispensing system 10 comprises dispensing device 20 and cap 24. Dispensing device 20 is opened at 29 and cap 24 is opened at 31. Dispensing device 20 comprises body 21, lead end 22, rear end 23 and passageway 27. Dispensing device 20 comprises additionally wall 28 that surrounds and defines compartment 30. Wall 28 is formed in a presently preferred embodiment of a semipermeable wall forming composition that is substantially permeable to the passage of an external fluid, and it is substantially impermeable to the passage of beneficial agent 32 and other ingredients present in compartment 30. Compartment 30 contains additionally a thermo-responsive means sensitive composition 33, identified by many lines, which thermo-responsive heat sensitive composition contains a beneficial agent 32, representative by dots. Compartment 30 further contains an expandable driving means 34 that is in contacted layered arrangement with thermo-responsive composition 33. Both the thermo-responsive composition and the expandable member possess a shape that corresponds to the internal shape of internal compartment 30. Compartment 30 contains also a dense member 35 or densifier that is in contact with thermo-sensitive composition 33, and it is positioned in the embodiment shown distant from expandable member 34. A passageway 36 extends through dense member 35 for delivering beneficial agent formulation 32 from dispensing device 20.

Expandable composition 33 is made from a hydrogel composition. The hydrogel can be noncross-linked, or optionally cross-linked, and it possesses the ability to imbibe and absorb fluid, and swell or expand to an enlarged state. The hydrogel is a polymeric composition and it swells or expands exhibiting a 2 to 50 fold volume increase. Hydrogels useful for this purpose include poly(hydroxyalkyl methacrylate), poly(ethylene oxide), agar and the like. The thermo-responsive composition 33 is formed in a presently preferred embodiment of a heat sensitive hyrdophobic or hydrophilic material that exhibits a solid-like property at a room temperature of 21° C., and within a few centigrade degrees thereof, and exhibits the ability to absorb heat and melt at the mammalian body temperature of 37° C., and within a few centigrade degrees thereof, usually 35° to 42° C. The thermo-responsive composition becomes dispensable in response to heat and acts as a carrier for drug composition 33 dispensed therein. Representative thermo-responsive compositions are cocoa butter, hydrogenated vegetable oil, triglyceride of saturated vegetable fatty acid, and the like. Dense member 35 is used in dispensing device 20 for keeping dispensing device 20 in the rumen-reticular sac of a ruminant. Generally dense member 35 well has a density of about 1 to 8, and it is formed from iron, iron shot coated with iron oxide, stainless steel and the like.

Cap 24 positioned over lead end 22 of dispensing device 20 comprises wall 37 that surrounds and forms an agent receiving space 38. Space 38 is formed by the interior surface of cap 24 and the exterior surface of dispensing device 20. Space 38 contains a beneficial agent formulation 39. Beneficial agent formulation 39 is available for immediate delivery when dispensing system 10 enters the animal of use. The term 'beneficial agent' as used herein for a beneficial agent, contained in the cap for immediate delivery, and in the dispensing device for controlled continuous delivery, includes drugs, nutrients, vitamins, food supplements, anthelminthics, antiparasitics, anti-infestants, and the like. Representative of beneficial agents include ivermectin, fenbendazole, pirantel, and the like. The amount of beneficial agent available for instant delivery is about 75 ng to 5 g, and the amount of beneficial agent available for controlled continuous delivery is about 250 mg to 25 g, or more.

Dispensing system 10 of FIG. 5, in operation in an animal, delivers beneficial agent formulation to the fluid environment of use by a combination of thermodynamic and kinetic integrally performed activities. That is, in operation as dispensing system 10 enters the gastrointestinal tract, cap 24 dissolves and immediately makes available beneficial agent formulation 39 for rapid use by the animal. Simultaneously with cap 24 dissolving and releasing formulation 39, dispensing device 20 is available for the continuous administration of beneficial agent formulation 32. In this operation, heat sensitive composition 33 in response to the temperature of the animal, particularly the rumen, absorbs energy, melts and forms a fluidic, or a semi-paste like deliverable composition for delivering through passageway 35 and passageway 27 to the rumen. As composition 33 absorbs thermal energy and melts, concomitantly external fluid is imbibed through external semipermeable wall 28 by expandable hydrophilic layered member 34 in a tendency towards osmotic equilibrium, to continuously expand hydrogel layer 34. Layer 34 expands, in a preferred embodiment while maintaining an intact immiscible boundary at interface 40 defined by heat-sensitive composition 33 and expandable layer 34. The expansion and swelling of layer 34 increases the volume of layer 34 and simultaneously layer 34 expands against beneficial agent composition 33 urging beneficial agent through the passageways to the exterior agent through the passageways to the exterior of dispensing device 20. The operations of dispensing device 20 enables device 20 to provide beneficial agent at a controlled rate over a prolonged period of time, usually 1 day to 6 months. Thus, dispensing, system 10 by the combined operations provides both instant and continuous beneficial agent to the environment of use.

FIG. 6 illustrates another dispensing system 10 provided by the invention. Dispensing system 10 comprises dispensing device 41 capped by cap 42. Dispensing device 42 is similar to the dispensing devices described in respect to FIGS. 3 through 5. In FIG. 6, a portion of dispensing device 41 is enclosed by cap 42 as seen in dashed lines, and it comprises photo-oriented laser drilled passageway 43. Cap 42 encloses instant available agent 44. Dispensing device 41 comprises also female receiving snap-fit member 45 that is an indentation around the body of device 41. The snap-fit indentation can embrace any geometric configuration and in the embodiment depicted snap-fit 45 is a circular indentation. Cap 42 comprises a male snap-fit member 46 that is an indentation or surface recess that extends around cap 42. Snap-fit 45 and snap-fit 46 have corresponding mating structures for positioning and release locking cap 42 onto and from dispensing device 41.

FIGS. 7 and 8 illustrate another embodiment provided by this invention. FIG. 7 depicts a dispensing system 10 comprising an outer capsule 50 formed of two parts comprising body 50a and a matching cap 50b telescopically joined to define a lumen 51 containing dispensing device 52. Optionally, capsule 50 can be a one piece capsule having a wall that surrounds an interior space containing a dispensing device. FIG. 8 depicts dispensing system 10 of FIG. 7 in opened view. In FIG. 8, dispensing system 10 comprises capsule cap 50, capsule cap 50b, internal space 51 containing beneficial agent formulation 53, and internal dispensing device 52. Dispensing device 52 comprises semipermeable wall 54, compartment 55, beneficial agent 56, expandable member 57, and prepositioned passageway 58. Dispensing system 10 delivers beneficial agent as previously described for the dispensing systems, supra.

The novel dispensing system of this invention provides instant beneficial agent formulation followed by continued beneficial agent formulation to an environment of use. While there has been described and pointed out features of the invention as applied to presently preferred embodiments, these skilled in the art will appreciate that various modification, changes, additions and omissions in the dispensing systems illustrated and described can be made without departing from the spirit of the invention.

I claim:

1. A dispensing system for delivering a beneficial agent formulation to an environment of use, the dispensing system comprising:

(a) a first means for delivering continously a beneficial agent formulation to an environment of use, said first means comprising:
  (1) a first wall that maintains its physical and chemical integrity in the environment of use and comprising in at least a part a polymeric composition permeable to the passage of fluid present in the environment of use, which wall surrounds and defines;
  (2) a compartment;
  (3) a beneficial agent in the compartment; and,
  (4) exit means in the wall for continuously delivering the beneficial agent formulation from the first means to the environment of use over a prolonged period of time; and,
(b) a second means for making a beneficial agent formulation instantly available to the environment of use, said second means comprising:
  (1) a second wall comprising a composition that loses its physical and chemical integrity in the environment of use for instantly making a beneficial agent formulation available to the environment of use, which wall telescopically caps, surrounds and encloses a portion of the first means and forms;
  (2) a lumen between the first means and the second means formed by the telescopically capped arrangement; and,
  (3) a beneficial agent formulation in the lumen available by the telescopically capped second wall losing its physical and chemical integrity in the environment of use for instant delivery of said beneficial agent by the second means to the environment of use.

2. The dispensing system for delivering the beneficial agent formulation to the environment of use according to claim 1, wherein the beneficial agent formulation in the compartment exhibitis an osmotic pressure gradient across the first wall against an external fluid, imbibes fluid through the wall and is osmotically delivered through the exit means for releasing the beneficial agent to the environment of use.

3. The dispensing system for delivering the beneficial agent formulation to the environment of use according to claim 1, wherein the compartment comprises an expandable member that absorbs fluid imbibed through the first wall into the compartment, expands and urges beneficial agent formulation through the exit means to the environment of use.

4. The dispensing system for delivering the beneficial agent formulation to the environment of use according to claim 1, where in the beneficial agent formulation in the compartment comprises a thermo-sensitive carrier that is solid at room temperature and dispensable through the exit means at the temperature of the environment of use.

5. The dispensing system for delivering the beneficial agent formulation to the environment of use according to claim 1, wherein the compartment comprises a dense member having a specific gravity greater than one for keeping the dispensing system in the environment of use.

6. A dispensing system for delivering a beneficial agent formulation to an environment of use, the dispensing system comprising:

(a) a first means for delivering continuously a beneficial agent formulation to an environment of use, said first means comprising:
  (1) a first wall comprising a composition that maintains its physical and chemical integrity in the environment of use and comprising at least in part a polymeric composition permeable to the passage of fluid present in the environment of use, which wall surrounds and defines;
  (2) a compartment;
  (3) a beneficial agent in the compartment; and,
  (4) means in the wall for continuously delivering the beneficial agent formulation from the first means to the environment of use over a prolonged period of time; and,
(b) a second means for making a beneficial agent formulation instantly available to the environment of use, said second means comprising:
  (1) a second wall comprising a composition that loses its physical and chemical integrity for instantly making a beneficial agent formulation available to the environment of use, which wall surrounds and encloses all of the first means and forms;
  (2) a lumem between the first means and the second means; and,
  (3) a beneficial agent formulation in the lumen available by the second wall losing its physical and chemical integrity in the environment of use for instant delivery of the beneficial agent to the environment of use.

7. The dispensing system for delivering the beneficial agent formulation to the environment of use according to claim 6, wherein the beneficial agent formulation in the compartment exhibits and osmotic pressure gradient across the first wall against an external fluid, imbibes fluid through the wall and is osmotically delivered through the means for releasing the beneficial agent to the environment of use.

8. The dispensing system for delivering the beneficial agent formulation to the environment of use according to claim 6, wherein the compartment comprises an expandable member that absorbs fluid imbibed through the wall into the compartment, expands and urges beneficial agent formulation through the exit means to the environment of use.

9. The dispensing system for delivering the beneficial agent formulation to the environment of use according to claim 6, wherein the beneficial agent formulation comprises a thermo-sensitive carrier that is solid at room temperature and dispensable through the exit means at the temperature of the environment of use.

10. The dispensing system for delivering the beneficial agent formulation to the environment of use according to claim 6, wherein the compartment comprises a dense member having a specific gravity greater than one for keeping the dispensing system in the environment of use.

11. The dispensing system for delivering the beneficial agent formulation to the environment of use according to claim 6, wherein the second wall comprises two parts for telescopically surrounding the first means.

12. The dispensing systen for delivering the beneficial agent formulation to the environment of use according to claim 6, wherein the second wall comprises a single piece.

* * * * *